(12) United States Patent
Ridden

(10) Patent No.: US 10,293,024 B2
(45) Date of Patent: May 21, 2019

(54) MAP KINASE P38 BINDING COMPOUNDS

(71) Applicant: Blueberry Therapeutics Limited, Macclesfield, Cheshire (GB)

(72) Inventor: John Ridden, Leek (GB)

(73) Assignee: Blueberry Therapeutics Limited, Macclesfield, Cheshire (GB)

( * ) Notice: Subject to any disclaimer, the term of this patent is extended or adjusted under 35 U.S.C. 154(b) by 0 days.

(21) Appl. No.: 14/911,658

(22) PCT Filed: Aug. 15, 2014

(86) PCT No.: PCT/GB2014/052514
§ 371 (c)(1),
(2) Date: Feb. 11, 2016

(87) PCT Pub. No.: WO2015/022549
PCT Pub. Date: Feb. 19, 2015

(65) Prior Publication Data
US 2016/0193281 A1 Jul. 7, 2016

(30) Foreign Application Priority Data
Aug. 15, 2013 (GB) .................................. 1314610.5

(51) Int. Cl.
| | | |
|---|---|---|
| *A61K 38/00* | (2006.01) | |
| *A61K 38/10* | (2006.01) | |
| *A61K 38/16* | (2006.01) | |
| *C07K 7/08* | (2006.01) | |
| *A61K 45/06* | (2006.01) | |
| *G01N 33/573* | (2006.01) | |

(52) U.S. Cl.
CPC .............. *A61K 38/10* (2013.01); *A61K 38/16* (2013.01); *A61K 45/06* (2013.01); *C07K 7/08* (2013.01); *G01N 33/573* (2013.01); *A61K 38/00* (2013.01); *G01N 2333/91205* (2013.01)

(58) Field of Classification Search
CPC ...................................................... A61K 38/00
See application file for complete search history.

(56) References Cited

U.S. PATENT DOCUMENTS

| | | | | | |
|---|---|---|---|---|---|
| 5,474,981 A | * | 12/1995 | Leder | ................... | C07K 14/522 514/19.3 |
| 7,906,149 B2 | * | 3/2011 | Yarborough | ......... | A61K 9/0014 424/520 |
| 2003/0119013 A1 | * | 6/2003 | Jiang | ...................... | C07K 14/38 435/6.13 |

FOREIGN PATENT DOCUMENTS

| | | | |
|---|---|---|---|
| CN | 1911958 A | 2/2007 | |
| WO | WO-0155420 A1 * | 8/2001 | ............... C12N 9/16 |
| WO | WO-2004069191 A2 * | 8/2004 | ......... G01N 33/5008 |
| WO | WO-2005012875 A2 * | 2/2005 | ............. C12Q 1/485 |
| WO | WO-2009/021137 A2 | 2/2009 | |
| WO | WO-2009/147368 A1 | 12/2009 | |
| WO | WO-2011/126882 A2 | 10/2011 | |
| WO | WO-2012/037397 A2 | 3/2012 | |
| WO | WO-2012/066376 A1 | 5/2012 | |

OTHER PUBLICATIONS

The MGC Program Team, "Generation and initial analysis of more than 15,000 full-length human and mouse cDNA sequences", PNAS, 2002, 16899-16903.*
Atp1a1a.3 protein [Danio rerio]; GenBank: AAH54591.; https://www.ncbi.nlm.nih.gov/protein/AAH54591.1; accessed Mar. 5, 2017; pp. 1-4.*
Science gateway, Protein Molecular Weight Calculator, www.sciencegateway.org/tools/proteinmw/htm; accessed on Oct. 31, 2017 (Year: 2017).*
Brazier et al., "Secondary structure analysis of the putative membrane-associated domains of the inward rectifier K+ channel ROMK1", Biochem J., 1998, 375-380 (Year: 1998).*
DNA/RNA/Protein Molecular Weight Calculator; http://www.currentprotocols.com/WileyCDA/CurPro3Tool/toolId-8.html; accessed on Mar. 12, 2018; 2 pages (Year: 2018).*
Wang et al., "Post-translational Modifications of Natural Antimicrobial Peptides and Strategies for Peptide Engineering", Current Biotechnology, 2012, pp. 72-79 (Year: 2012).*
Chang et al., Crystal Structures of MAP Kinase p38 Complexed to the Docking Sites on Its Nuclear Substrate MEF2A and Activator MKK3b, Molecular Cell, vol. 9(6):1241-1249, Jun. 2002.
International Search Report issued on corresponding International Patent Application No. PCT/GB2014/052514, dated Oct. 31, 2014.

* cited by examiner

*Primary Examiner* — Lianko G Garyu
(74) *Attorney, Agent, or Firm* — Howson & Howson LLP

(57) ABSTRACT

A compound comprising the amino acid sequence HKSRALLIFQKIMWLRRQ (SEQ ID No: 1) or comprising a part of said amino acid sequence of 7 or more amino acids, or comprising a variant of said amino acid sequence or said part thereof in which from 1 to 5 amino acids have been altered, wherein the compound binds to MAP kinase p38α. The compounds are useful in binding to and inhibiting MAP kinase p38α, and are useful as research tools, in drug discovery, medicine, particularly for treating inflammatory conditions.

Figure 3:
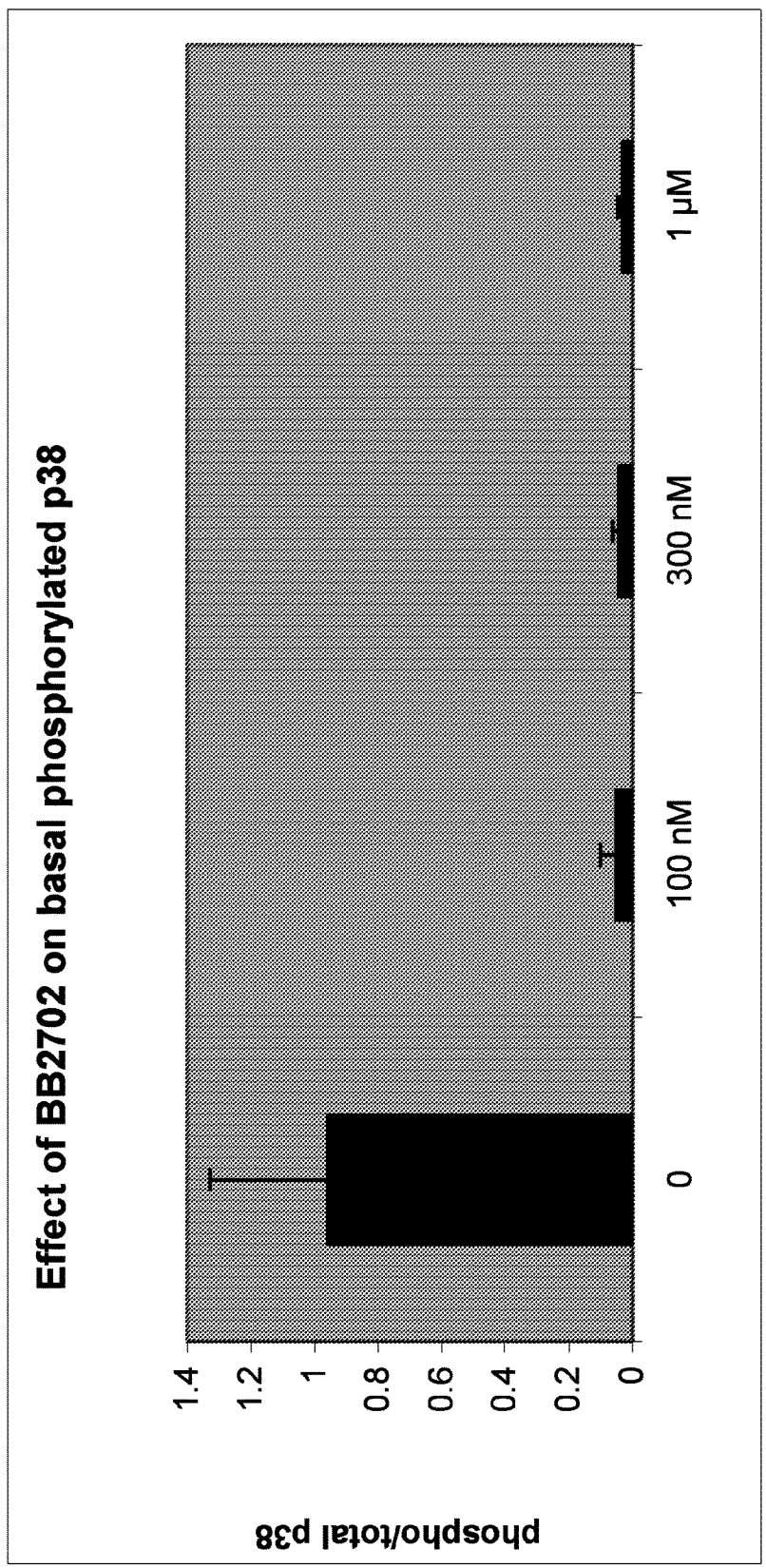

21 Claims, 5 Drawing Sheets
Specification includes a Sequence Listing.

Figure 1

| | | | |
|---|---|---|---|
| 1 | MSQERPTFYRQELNKTIWEVPERYQNLSPVGSSGSGAYGSVCAAFDTKTGLRVAVKKLSRPFQ | 60 | Q16539 MK14_HUMAN |
| 1 | MSQERPTFYRQELNKTIWEVPERYQNLSPVGSSGSGAYGSVCAAFDTKTGLRVAVKKLSRPFQ | 60 | O02812 MK14_CANFA |
| | ************************************************************ | | |
| 61 | SIIHAKRTYRELRLLKHMKHENVIGLLDVFTPARSLEEFNDVYLVTHLMGADLNNIVKCQ | 120 | Q16539 MK14_HUMAN |
| 61 | SIIHAKRTYRELRLLKHMKHENVIGLLDVFTPARSLEEFNDVYLVTHLMGADLNNIVKCQ | 120 | O02812 MK14_CANFA |
| | ************************************************************ | | |
| 121 | KLTDDHVQFLIYQILRGLKYIHSADIIHRDLKPSNLAVNEDCELKILDFGLARHTDDEMT | 180 | Q16539 MK14_HUMAN |
| 121 | KLTDDHVQFLIYQILRGLKYIHSADIIHRDLKPSNLAVNEDCELKILDFGLARHTDDEMT | 180 | O02812 MK14_CANFA |
| | ************************************************************ | | |
| 181 | GYVATRWYRAPEIMLNWMHYNQTVDIWSVGCIMAELLTGRTLFPGTDHIDQLKLILRLVG | 240 | Q16539 MK14_HUMAN |
| 181 | GYVATRWYRAPEIMLNWMHYNQTVDIWSVGCIMAELLTGRTLFPGTDHIDQLKLILRLVG | 240 | O02812 MK14_CANFA |
| | ************************************************************ | | |
| 241 | TPGAELLKKISSESARNYIQSLTQMPKMNFANVFIGANPLAVDLLEKMLVLDSDKRITAA | 300 | Q16539 MK14_HUMAN |
| 241 | TPGADLLKKISSESARNYIQSLTQMPKMNFANVFIGANPLAVDLLEKMLVLDSDKRITAA | 300 | O02812 MK14_CANFA |
| | ************************************************************ | | |
| 301 | QALAHAYFAQYHDPDDEPVADPYDQSFESRDLLIDEWKSLTYDEVISFVPPPLDQEEMES | 360 | Q16539 MK14_HUMAN |
| 301 | QALAHAYFAQYHDEDDEPVADPYDQSFESRDLLIDEWKSLTYDEVVSFVPPPLDQEEMES | 360 | O02812 MK14_CANFA |
| | ************************************************************ | | |

Q16539 MK14_HUMAN = SEQ ID No: 18
O02812 MK14_CANFA = SEQ ID No: 19

Figure 2
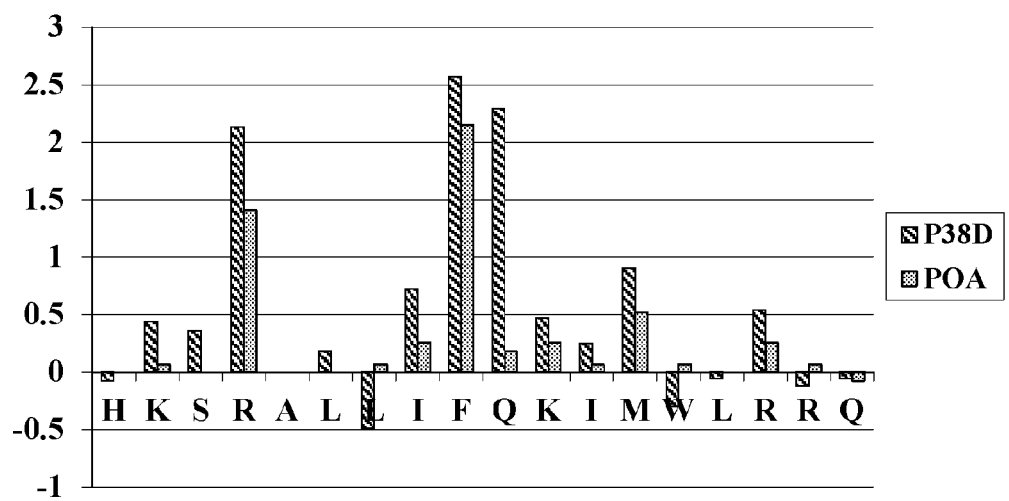
Alanine Scanning : Log($K_{mutant}$) −Log($K_{parent}$)
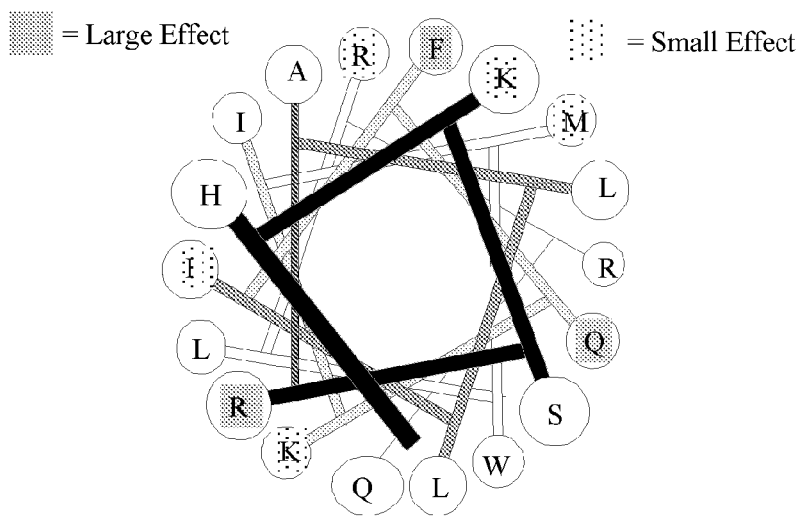
Alanine Scanning : Helical Wheel

```
                       SEQUENCE LISTING

<160> NUMBER OF SEQ ID NOS: 25

<210> SEQ ID NO 1
<211> LENGTH: 18
<212> TYPE: PRT
<213> ORGANISM: Artificial Sequence
<220> FEATURE:
<223> OTHER INFORMATION: Peptide

<400> SEQUENCE: 1

His Lys Ser Arg Ala Leu Leu Ile Phe Gln Lys Ile Met Trp Leu Arg
1               5                   10                  15

Arg Gln

<210> SEQ ID NO 2
<211> LENGTH: 17
<212> TYPE: PRT
<213> ORGANISM: Artificial Sequence
<220> FEATURE:
<223> OTHER INFORMATION: Peptide

<400> SEQUENCE: 2

His Lys Ser Arg Ala Leu Leu Ile Phe Gln Lys Ile Met Trp Leu Arg
1               5                   10                  15

Arg

<210> SEQ ID NO 3
<211> LENGTH: 16
<212> TYPE: PRT
<213> ORGANISM: Artificial Sequence
<220> FEATURE:
<223> OTHER INFORMATION: Peptide

<400> SEQUENCE: 3

His Lys Ser Arg Ala Leu Leu Ile Phe Gln Lys Ile Met Trp Leu Arg
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Peptide

<400> SEQUENCE: 4

His Lys Ser Arg Ala Leu Leu Ile Phe Gln Lys Ile Met Trp Leu
1               5                   10                  15

<210> SEQ ID NO 5
<211> LENGTH: 14
<212> TYPE: PRT
<213> ORGANISM: Artificial Sequence
<220> FEATURE:
<223> OTHER INFORMATION: Peptide

<400> SEQUENCE: 5
```

His Lys Ser Arg Ala Leu Leu Ile Phe Gln Lys Ile Met Trp
1               5                   10

<210> SEQ ID NO 6
<211> LENGTH: 17
<212> TYPE: PRT
<213> ORGANISM: Artificial Sequence
<220> FEATURE:
<223> OTHER INFORMATION: Peptide

<400> SEQUENCE: 6

Lys Ser Arg Ala Leu Leu Ile Phe Gln Lys Ile Met Trp Leu Arg Arg
1               5                   10                  15

Gln

<210> SEQ ID NO 7
<211> LENGTH: 16
<212> TYPE: PRT
<213> ORGANISM: Artificial Sequence
<220> FEATURE:
<223> OTHER INFORMATION: Peptide

<400> SEQUENCE: 7

Ser Arg Ala Leu Leu Ile Phe Gln Lys Ile Met Trp Leu Arg Arg Gln
1               5                   10                  15

<210> SEQ ID NO 8
<211> LENGTH: 11
<212> TYPE: PRT
<213> ORGANISM: Artificial Sequence
<220> FEATURE:
<223> OTHER INFORMATION: Peptide

<400> SEQUENCE: 8

Ser Arg Ala Leu Leu Ile Phe Gln Lys Ile Met
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Peptide

<400> SEQUENCE: 9

Ser Arg Ala Leu Leu Ile Phe Gln
1               5

<210> SEQ ID NO 10
<211> LENGTH: 11
<212> TYPE: PRT
<213> ORGANISM: Artificial Sequence
<220> FEATURE:
<223> OTHER INFORMATION: Peptide

<400> SEQUENCE: 10

His Ala Leu Ala Ile Phe Gln Lys Ile Met Trp
1               5                   10

<210> SEQ ID NO 11
<211> LENGTH: 18
<212> TYPE: PRT
<213> ORGANISM: Artificial Sequence
<220> FEATURE:
<223> OTHER INFORMATION: Peptide -continued

```
<400> SEQUENCE: 11

His Lys Ser Arg Ala Leu Ala Ile Phe Gln Lys Ile Met Ala Leu Arg
1               5                   10                  15

Arg Gln

<210> SEQ ID NO 12
<211> LENGTH: 18
<212> TYPE: PRT
<213> ORGANISM: Artificial Sequence
<220> FEATURE:
<223> OTHER INFORMATION: Peptide

<400> SEQUENCE: 12

Ala Lys Ser Arg Ala Leu Leu Ile Phe Gln Lys Ile Met Trp Leu Arg
1               5                   10                  15

Arg Gln

<210> SEQ ID NO 13
<211> LENGTH: 18
<212> TYPE: PRT
<213> ORGANISM: Artificial Sequence
<220> FEATURE:
<223> OTHER INFORMATION: Peptide

<400> SEQUENCE: 13

His Lys Ser Arg Ala Ala Leu Ile Phe Gln Lys Ile Met Trp Leu Arg
1               5                   10                  15

Arg Gln

<210> SEQ ID NO 14
<211> LENGTH: 18
<212> TYPE: PRT
<213> ORGANISM: Artificial Sequence
<220> FEATURE:
<223> OTHER INFORMATION: Peptide

<400> SEQUENCE: 14

His Lys Ser Arg Ala Leu Leu Ile Phe Gln Lys Ile Met Trp Ala Arg
1               5                   10                  15

Arg Gln

<210> SEQ ID NO 15
<211> LENGTH: 18
<212> TYPE: PRT
<213> ORGANISM: Artificial Sequence
<220> FEATURE:
<223> OTHER INFORMATION: Peptide

<400> SEQUENCE: 15

His Lys Ser Arg Ala Leu Leu Ile Phe Gln Lys Ile Met Trp Leu Arg
1               5                   10                  15

Ala Gln

<210> SEQ ID NO 16
<211> LENGTH: 18
<212> TYPE: PRT
<213> ORGANISM: Artificial Sequence
<220> FEATURE:
<223> OTHER INFORMATION: Peptide

<400> SEQUENCE: 16

His Lys Ser Arg Ala Leu Leu Ile Phe Gln Lys Ile Met Trp Leu Arg
1               5                   10                  15
```

Arg Ala

<210> SEQ ID NO 17
<211> LENGTH: 10
<212> TYPE: PRT
<213> ORGANISM: Artificial Sequence
<220> FEATURE:
<223> OTHER INFORMATION: Peptide

<400> SEQUENCE: 17

Ser Arg Ala Leu Leu Ile Phe Gln Lys Ile
1               5                   10

<210> SEQ ID NO 18
<211> LENGTH: 360
<212> TYPE: PRT
<213> ORGANISM: Homo sapiens

<400> SEQUENCE: 18

Met Ser Gln Glu Arg Pro Thr Phe Tyr Arg Gln Glu Leu Asn Lys Thr
1               5                   10                  15

Ile Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly Leu
        35                  40                  45

Arg Val Ala Val Lys Lys Leu Ser Arg Pro Phe Gln Ser Ile Ile His
50                  55                  60

Ala Lys Arg Thr Tyr Arg Glu Leu Arg Leu Leu Lys His Met Lys His
65                  70                  75                  80

Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
        115                 120                 125

Phe Leu Ile Tyr Gln Ile Leu Arg Gly Leu Lys Tyr Ile His Ser Ala
130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205

Val Gly Cys Ile Met Ala Glu Leu Leu Thr Gly Arg Thr Leu Phe Pro
210                 215                 220

Gly Thr Asp His Ile Asp Gln Leu Lys Leu Ile Leu Arg Leu Val Gly
225                 230                 235                 240

Thr Pro Gly Ala Glu Leu Leu Lys Lys Ile Ser Ser Glu Ser Ala Arg
                245                 250                 255

Asn Tyr Ile Gln Ser Leu Thr Gln Met Pro Lys Met Asn Phe Ala Asn
            260                 265                 270

Val Phe Ile Gly Ala Asn Pro Leu Ala Val Asp Leu Leu Glu Lys Met
        275                 280                 285

Leu Val Leu Asp Ser Asp Lys Arg Ile Thr Ala Ala Gln Ala Leu Ala

```
            290                 295                 300
His Ala Tyr Phe Ala Gln Tyr His Asp Pro Asp Glu Pro Val Ala
305                 310                 315                 320

Asp Pro Tyr Asp Gln Ser Phe Glu Ser Arg Asp Leu Leu Ile Asp Glu
                325                 330                 335

Trp Lys Ser Leu Thr Tyr Asp Glu Val Ile Ser Phe Val Pro Pro Pro
                340                 345                 350

Leu Asp Gln Glu Glu Met Glu Ser
                355                 360

<210> SEQ ID NO 19
<211> LENGTH: 360
<212> TYPE: PRT
<213> ORGANISM: Canis lupus

<400> SEQUENCE: 19

Met Ser Gln Glu Arg Pro Thr Phe Tyr Arg Gln Glu Leu Asn Lys Thr
1               5                   10                  15

Ile Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly Leu
        35                  40                  45

Arg Val Ala Val Lys Lys Leu Ser Arg Pro Phe Gln Ser Ile Ile His
50                  55                  60

Ala Lys Arg Thr Tyr Arg Glu Leu Arg Leu Leu Lys His Met Lys His
65                  70                  75                  80

Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
        115                 120                 125

Phe Leu Ile Tyr Gln Ile Leu Arg Gly Leu Lys Tyr Ile His Ser Ala
130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205

Val Gly Cys Ile Met Ala Glu Leu Leu Thr Gly Arg Thr Leu Phe Pro
210                 215                 220

Gly Thr Asp His Ile Asp Gln Leu Lys Leu Ile Leu Arg Leu Val Gly
225                 230                 235                 240

Thr Pro Gly Ala Asp Leu Leu Lys Lys Ile Ser Ser Glu Ser Ala Arg
                245                 250                 255

Asn Tyr Ile Gln Ser Leu Thr Gln Met Pro Lys Met Asn Phe Ala Asn
            260                 265                 270

Val Phe Ile Gly Ala Asn Pro Leu Ala Val Asp Leu Leu Glu Lys Met
        275                 280                 285

Leu Val Leu Asp Ser Asp Lys Arg Ile Thr Ala Ala Gln Ala Leu Ala
290                 295                 300
```

```
His Ala Tyr Phe Ala Gln Tyr His Asp Pro Asp Glu Pro Val Ala
305                 310                 315                 320

Asp Pro Tyr Asp Gln Ser Phe Glu Ser Arg Asp Leu Leu Ile Asp Glu
            325                 330                 335

Trp Lys Ser Leu Thr Tyr Asp Glu Val Val Ser Phe Val Pro Pro Pro
            340                 345                 350

Leu Asp Gln Glu Glu Met Glu Ser
            355                 360

<210> SEQ ID NO 20
<211> LENGTH: 11
<212> TYPE: PRT
<213> ORGANISM: Artificial Sequence
<220> FEATURE:
<223> OTHER INFORMATION: Peptide

<400> SEQUENCE: 20

Arg Ala Leu Leu Ile Phe Gln Lys Ile Met Trp
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Peptide

<400> SEQUENCE: 21

Arg Ala Leu Leu Ile Phe Gln
1               5

<210> SEQ ID NO 22
<211> LENGTH: 10
<212> TYPE: PRT
<213> ORGANISM: Artificial Sequence
<220> FEATURE:
<223> OTHER INFORMATION: Peptide

<400> SEQUENCE: 22

Arg Ala Leu Leu Ile Phe Gln Lys Ile Met
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Peptide
<220> FEATURE:
<221> NAME/KEY: VARIANT
<222> LOCATION: (1)..(1)
<223> OTHER INFORMATION: R, K, Q, OR H
<220> FEATURE:
<221> NAME/KEY: VARIANT
<222> LOCATION: (4)..(4)
<223> OTHER INFORMATION: L, A, V, I, OR L
<220> FEATURE:
<221> NAME/KEY: VARIANT
<222> LOCATION: (6)..(6)
<223> OTHER INFORMATION: F, Y, OR H
<220> FEATURE:
<221> NAME/KEY: VARIANT
<222> LOCATION: (7)..(7)
<223> OTHER INFORMATION: Q, N, K, OR R
<220> FEATURE:
<221> NAME/KEY: VARIANT
<222> LOCATION: (11)..(11)
<223> OTHER INFORMATION: W, A, V, I, or L
```

```
<400> SEQUENCE: 23

Xaa Ala Leu Xaa Ile Xaa Xaa Lys Ile Met Xaa
1               5                   10

<210> SEQ ID NO 24
<211> LENGTH: 6
<212> TYPE: PRT
<213> ORGANISM: Artificial Sequence
<220> FEATURE:
<223> OTHER INFORMATION: Peptide

<400> SEQUENCE: 24

Leu Ile Phe Gln Lys Ile
1               5

<210> SEQ ID NO 25
<211> LENGTH: 13
<212> TYPE: PRT
<213> ORGANISM: Artificial Sequence
<220> FEATURE:
<223> OTHER INFORMATION: Peptide

<400> SEQUENCE: 25

Arg Lys Pro Asp Leu Arg Val Val Ile Pro Pro Ser Ser
1               5                   10
```

MAP KINASE P38 BINDING COMPOUNDS

CROSS-REFERENCE TO RELATED APPLICATIONS

This application is a US national phase of International Patent Application No. PCT/GB2014/052514, filed Aug. 15, 2014, which claims the benefit of priority of GB 1314610.5, filed Aug. 15, 2013, which applications are incorporated herein by reference in their entirety.

The present invention relates to compounds and their uses. In particular, it relates to peptides and their uses in inhibiting mitogen-activated protein kinase p38 alpha (short name MAP kinase p38α) and in treating inflammatory conditions.

For the avoidance of doubt, for the most part the term MAP kinase p38α will be used throughout this specification. However, the enzyme is also known by the following recommended name and terms: mitogen-activated protein kinase 14 (short names MAP kinase 14 and MAPK 14) and IUB classification EC 2.2.11.24. It also has the alternative names: cytokine suppressive anti-inflammatory drug-binding protein (short name CSAID-binding protein and CSBP), MAP kinase MXI2, MAX-interacting protein 2, and stress-activated protein kinase 2a (short name SAPK2a). The enzyme also has the Uniprot identifier Q16539. The enzyme is also sometimes called p38α in the specification.

The listing or discussion of an apparently prior-published document in this specification should not necessarily be taken as an acknowledgement that the document is part of the state of the art or is common general knowledge.

MAP kinase p38α plays a central role in inflammation and it has been the subject of extensive efforts in both basic research and drug discovery. Schieven (2009) *Curr. Top. Med. Chem.* 9, 1038-1048 summarizes the biology of the p38 kinase with a focus on its role in inflammation. The p38 kinase regulates the production of key inflammatory mediators by cells of the innate immune system, including TNFalpha, IL-1beta, and COX-2. In addition, p38 also acts downstream of cytokines such as TNFalpha, mediating some of their effects. Recently p38 has also been found to play a role in responses of T cells, including Th17 and regulatory T cells. Consistent with its important role in inflammation, recent evidence suggests cells may utilize a variety of feedback mechanisms to regulate and maintain p38 signal transduction. The biological processes regulated by p38 kinase suggest both a wide variety of potential indications for inhibitors and a level of complexity that has proven challenging to drug discovery efforts around this target.

Karcher & Laufer (2009) *Curr. Top. Med. Chem.* 9, 655-676 notes that since 1993 an immense number of inhibitors of p38 MAP kinase have been characterized. Aside from the well known pyridinylimidazoles, multiple novel scaffolds have been identified, but only a small number have advanced into clinical phase II studies, probably due to high toxicity and poor selectivity. According to Karcher & Laufer, to gain safe drug profiles, high potency, marginal CYP450 (cytochrome P450) interaction and toxicity, as well as high levels of selectivity would be desirable.

The crystal structures of MAP kinase p38α complexed to the docking sites on its nuclear substrate MEF2A and activator MKK3b are known (Chang et al (2002) *Cell* 9, 1241-1249).

Previous small molecule inhibitors have suffered from a lack of selectivity for MAP kinase p38α and also from a range of toxicities in human clinical trials, including significant liver toxicity. To the inventor's knowledge, no MAP kinase p38α compound has successfully reached market, with most failing in phase IIb human clinical trials.

MAP Kinase p38α plays a central role in the inflammation signalling cascade and therefore its inhibition is believed to have a beneficial role in a range of human disease indications, especially inflammatory conditions. These include, but are not limited to, inflammatory disorders of the skin such as atopic dermatitis, psoriasis, acne vulgaris, dermal scarring. Activation of MAP kinase p38α may also play a fundamental role in other disorders involving inflammation including, constrictive obstructive pulmonary disease, asthma, inflammatory bowel disease, atherosclerosis, cancer and rheumatoid arthritis.

The invention described herein provides compounds which are useful in binding to and inhibiting MAP kinase p38α, and are useful as research tools, in drug discovery and in human and veterinary medicine, particularly for treating inflammatory conditions. Such inflammatory conditions may exist in a range of mammals, including man and dogs. Advantageously, compounds are provided that are selective for MAP kinase p38α and do not substantially bind to, or inhibit, other protein kinases.

WO 2009/021137 relates to various kinase inhibiting peptides. WO 2011/126882 relates to anti-inflammatory D3 peptides.

A first aspect of the invention provides a compound comprising the amino acid sequence HKSRALLIFQKIMWLRRQ (SEQ ID No: 1) or comprising a part of said amino acid sequence of 7 or more amino acids or comprising a variant of said amino acid sequence or of said part thereof in which from 1 to 5 amino acids have been altered, wherein the compound binds to MAP kinase p38α.

The IUB/IUPAC one letter code for amino acids is used throughout the specification unless otherwise noted, and the amino acid sequence is given in the conventional N- to C-terminal direction. Typically, the amino acids are L-amino acids, but as noted below, in some embodiments of the invention some of them may be D-amino acids. The altered amino acids in the variants are typically naturally occurring amino acids, which include the 20 amino acids that are encoded by the genetic code, and also include other natural amino acids such as hydroxyproline, selenomethionine, and carnitine. However, in some embodiments one or more of the altered amino acids may be non-natural amino acids such as allylalanine and diphenylalanine.

Typically, when an amino acid in SEQ ID No: 1 or a part thereof is altered it is changed to a conservative amino acid. For example, amino acids within the following groups of amino acids are considered to be conservative alterations: (N, Q); (K, R); (S, T); (I, L, M); (F, Y). Thus, conveniently an I amino acid residue may be altered to a L amino acid residue or a N amino acid residue may be altered to a Q amino acid residue in the compound, and/or a K amino acid residue may be altered to a R amino acid residue in the compound, and so on.

The compound of the first aspect of the invention conveniently may comprise 7, 8, 9, 10, 11, 12, 13, 14, 15, 16 or 17 contiguous amino acids from SEQ ID No: 1, or may comprise a variant of said 7 to 17, or all 18, contiguous amino acids from SEQ ID No: 1 in which from 1 to 5 amino acids are altered. Typically, 1, 2, 3, 4 or 5 amino acids may be altered in the amino acid sequence SEQ ID No: 1, or the part thereof from 7 to 17 amino acids, present in the compound. It is preferred that if the part thereof contains 15 contiguous amino acids or fewer (such as 11, 12, 13, 14 or 15 amino acids), no more than four amino acids are altered (such as three, two, one or zero). It is also preferred that if the part thereof contains 10 contiguous amino acids or fewer (such as 9 or 10), no more than three amino acids are altered (such as two, one or zero). It is also preferred that if the part thereof contains seven or eight contiguous amino acids, no more than two amino acids are altered (such as one or zero). It is preferred that no more than around 25% in number of the amino acid residues of SEQ ID No: 1 or of the part thereof are altered. It is further preferred that no more than around 20% or 15% in number of the amino acid residues of SEQ ID No: 1 or of the part thereof are altered. The % can be calculated by determining the number of altered amino acid residues compared to SEQ ID No: 1 or the appropriate part thereof, dividing by the number of amino acid residues in the part corresponding to SEQ ID No: 1 and multiplying by 100. For example, the peptide HALAIFQKIMW (SEQ ID NO: 10) has two amino residues (underlined, bold) which differ from the part of SEQ ID No: 1 with which it can be prepared, namely RALLIFQKIMW (SEQ ID NO: 20). Thus, the % of altered residues is calculated as 2/11 × 100% =18.2%.

Preferably, the compound of the first aspect of the invention comprises the amino acid sequence RXXXXFQ, wherein X is any amino acid. More preferably, the compound of the first aspect of the invention comprises the amino acid sequence RALLIFQ (SEQ ID NO: 21). Still more preferably, the compound of the first aspect of the invention comprises the amino acid sequence RALLIFQ-KIM (SEQ ID NO: 22).

In one embodiment, the compound according to the first aspect of the invention may be represented as $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$. Preferably, $X_4$ may be R, K, Q or H, $X_9$ may be F, Y or H, $X_{10}$ may be Q, N, K or R. Preferably the compound is one in which $X_4$ is R, $X_9$ is F or $X_{10}$ is Q. More preferably the compound is one in which $X_4$ is R, $X_9$ is F and $X_{10}$ is Q.

It is preferred that at least 3 of the following occur in the compound: $X_1$ is H, $X_2$ is K, $X_3$ is S, $X_5$ is A, $X_6$ is L, $X_7$ is L, $X_8$ is I, $X_{11}$ is K, $X_{12}$ is I, $X_{13}$ is M, $X_{14}$ is W, $X_{15}$ is L, $X_{16}$ is R, $X_{17}$ is R, and $X_{18}$ is Q. It is preferred if at least 4 or 5 or 6 or 7 or 8 or 9 or 10 or 11 or 12 or 13 or 14 of the immediately preceding amino acid positions occur in the compound.

It is particularly preferred if the compound is one wherein $X_2$ is K, $X_8$ is I, $X_{13}$ is M or $X_{16}$ is R. It is particularly preferred if the compound is one wherein $X_2$ is K, $X_8$ is I, $X_{13}$ is M and $X_{16}$ is R.

Compounds of the invention also include those in which $X_1$ is A, V, I or L, $X_2$ is A, R, I or L, $X_3$ is A, V, S, T, N or Q, $X_4$ is R, K, Q or H, $X_5$ is A, V, I or L, $X_6$ is L, I, A or V, $X_7$ is A, V, I or L, $X_8$ is A, V, I or L, $X_9$ is F, Y or H, $X_{10}$ is Q, N, K or R, $X_{11}$ is K, Q or R, $X_{12}$ is I, L, V or A, $X_{13}$ is M, L, I, C, $X_{14}$ is W, A, V, I, L, M or F, $X_{15}$ is L, I, A or V, $X_{16}$ is A, V, I, L, R, K, Q or H, $X_{17}$ is A, V, I or L, and/or $X_{18}$ is Q, A, V, I or L.

It will also be appreciated that in the embodiments in which the compound comprises fewer than 18 amino acid residues of SEQ ID No: 1, certain position X may be "null" (ie do not contain an amino acid residue). Thus, for example, when the compound comprises a part of SEQ ID No: 1 of 17 contiguous amino acid residues, either $X_1$ is null or $X_{18}$ is null. Similarly, when the compound comprises a part of SEQ ID No: 1 of 16 contiguous amino acid residues, $X_1$ and $X_2$, or $X_1$ and $X_{18}$ or $X_{17}$ and $X_{18}$ are null, and so on for parts of SEQ ID No: 1 of contiguous amino acid residues.

It is preferred that the amino acid sequence of the compound of the first or second aspect of the invention has from 7 to 18 amino acids. For example, the amino acid sequence may have 8, 9, 10, 11, 12, 13, 14, 15, 16 or 17 amino acids. It is preferred if the compound has from 8 to 18 amino acids. It is also preferred if the compound has from 11 to 18 amino acids. Typically when the compound of the first or second aspect of the invention consists of a peptide it has a molecular weight of less than 30 000 daltons, preferably less than 25 000 daltons, more preferably less than 20 000 daltons. Typically, when the compound of the first or second aspect of the invention comprises a peptide portion linked to another moiety as discussed below, the compound of the invention may typically have a molecular weight of between 10 000 daltons and 100 000 daltons, such as between 20 000 daltons and 80 000 daltons, for example between 20 000 daltons and 50 000 daltons.

Compounds of the invention include those that comprise or consist of the amino acid sequence (R, K, Q, H) A L (L, A, V, I, L) I (F, Y, H) (Q, N, K, R) K I M (W, A, V, I, L) SEQ ID NO: 23) wherein one amino acid from each set in parentheses is used in that position and wherein the compound binds to MAP kinase p38α. Thus, the invention includes compounds comprising the amino acid sequence $X_4X_5$-$X_6$-$X_7$-$X_8$-$X_9$-$X_{10}$-$X_{11}$-$X_{12}$-$X_{13}$-$X_{14}$ wherein $X_4$ is R, K, Q or H, $X_5$ is A, $X_6$ is L, $X_7$ is L, A, V, I or L, $X_8$ is I, $X_9$ is F, Y or H, $X_{10}$ is Q, N, K or R, $X_{11}$ is K, $X_{12}$ is I, $X_{13}$ is M and $X_{14}$ is W, A, V, I or L wherein the compound binds to MAP kinase p38α. In this embodiment, each of $X_1$, $X_2$, $X_3$, $X_{15}$, $X_{16}$, $X_{17}$ and $X_{18}$ are "null" (ie no amino acid residue present at that position).

Compounds of the invention include HKSRALLIFQ-KIMWLRRQ (SEQ ID No: 1), HKSRALLIFQKIMWLRR (SEQ ID No: 2), HKSRALLIFQKIMWLR (SEQ ID No: 3), HKSRALLIFQKIMWL (SEQ ID No: 4), HKSRALLIFQ-KIMW (SEQ ID No: 5), KSRALLIFQKIMWLRRQ (SEQ ID No: 6), SRALLIFQKIMWLRRQ (SEQ ID No: 7), SRALLIFQKIM (SEQ ID No: 8), SRALLIFQ (SEQ ID No: 9), HALAIFQKIMW (SEQ ID No: 10), HKSRALAIFQKI-MALRRQ (SEQ ID No: 11), AKSRALLIFQKIMWLRRQ (SEQ ID No: 12), HKSRAALIFQKIMWLRRQ (SEQ ID No: 13), HKSRALLIFQKIMWARRQ (SEQ ID No: 14), HKSRALLIFQKIMWLRAQ (SEQ ID No: 15), HKSRAL-LIFQKIMWLRRA (SEQ ID No: 16) and SRALLIFQKI (SEQ ID No: 17).

The amino acid sequences of the compounds of the invention are peptides, by which term we include compounds that have amino acid residues (H-Cα-[side chain]) but which may be joined by peptide (—CO—NH—) or non-peptide linkages as is discussed below.

Peptides may be synthesised by the Fmoc-polyamide mode of solid-phase peptide synthesis as disclosed by Lu et al (1981) *J. Org. Chem.* 46, 3433, incorporated herein by reference, and references therein. Reagents for peptide synthesis are readily commercially available.

Purification of the compounds of the invention may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

A preferred compound of the invention consists of the amino acid sequence HKSRALLIFQKIMWLRRQ (SEQ ID No: 1) or a part of said amino acid sequence of 7 or more amino acids or comprising a variant of said amino acid sequence or of said part thereof in which from 1 to 5 amino acids have been altered, wherein the compound binds to MAP kinase p38α. Further preferences are the same as above. As discussed below, it is preferred if the compounds of the invention are N-acetylated; it is particularly preferred that the compound consisting of the amino acid sequence HKSRALLIFQKIMWLRRQ (SEQ ID No: 1) is N-acetylated. The compound which consists of the amino acid sequence HKSRALLIFQKIMWLRRQ (SEQ ID No: 1) and which is N-acetylated has been given the code name BB2702 when all of the amino acids are L-amino acids and there are peptide bonds between all the amino acid residues.

The compound of the invention may contain at least one D-amino acid residue, such as 1, 2 or 3 or 4 or 5 or 6 or 7 or 8 D-amino acids. Typically, the compound of the invention contains 0, 1, 2 or 3 D-amino acids. The presence of D-amino acids in the compound of the invention may be useful in preventing degradation of the compound by proteases. Other methods for making peptides resistant to proteolytic degradation include blocking the N- and/or C-terminal amino acid residues. Thus, in some embodiments the N-and/or C-terminal amino acid residues are blocked. Suitable blocking methods include acetylation of the N-terminus or incorporating a pyroglutamate residue at the N-terminus.

There are a number of different approaches to the design and synthesis of peptide compounds that do not contain amide bonds. In one approach, such as disclosed by Sherman & Spatola (1990) *J. Am. Chem. Soc.* 112, 433, incorporated herein by reference, one or more amide bonds have been replaced in an essentially isoteric manner by a variety of chemical functional groups.

Retro-inverso peptidomimetics, in which the peptide bonds are reversed, can be synthesised by methods known in the art, for example such as those described in Mézière et al (1997) *J. Immunol.* 159 3230-3237, incorporated herein by reference. This approach involves making pseudopeptides containing changes involving the backbone, and not the orientation of side chains. Retro-inverse peptides, which contain NH—CO bonds instead of CO—NH peptide bonds, are more resistant to proteolysis.

It may be advantageous to introduce a cyclic moiety into a peptide-based framework. The cyclic moiety restricts the conformational space of the peptide structure and this may lead to an increased affinity of the peptide for MAP kinase p38α. An added advantage of this strategy is that the introduction of a cyclic moiety into a peptide may also result in the peptide having a diminished sensitivity to cellular peptidases.

Although it is preferred if the compound of the invention is a peptide as defined, in some embodiments of the invention the compound consists of a peptide joined to another moiety. Convenient moieties to which the peptide may be joined include polyethylene glycol (PEG) and peptide sequences, such as TAT and antennapedia which enhance delivery to cells.

PEGylation is a method well known to those skilled in the art wherein a (peptide or other compound) is modified such that one or more polyethylene glycol (PEG) molecules are covalently attached to the side chain of one or more amino acids. It is one of the most important molecule altering structural chemistry techniques (MASC). Other MASC techniques may be used; such techniques may improve the pharmacodynamic properties of a compound, for example extending its serum half life in vivo. A PEG-peptide conjugate is formed by first activating the PEG moiety so that it will react with, and couple to, the compound of the invention. PEG moieties vary considerably in molecular weight and conformation, with the early moieties (monofunctional PEGs; mPEGs) being linear with molecular weights of 12 kDa or less, and later moieties being of increased molecular weights. PEG2, a recent innovation in PEG technology, involves the coupling of a 30 kDa (or less) mPEG to a lysine amino acid (although PEGylation can be extended to the addition of PEG to other amino acids) that is further reacted to form a branched structure that behaves like a linear mPEG of much greater molecular weight (Kozlowski et al., (2001), *Biodrugs* 15, 419-429). Methods that may be used to covalently attach the PEG molecules to the compounds of the invention are further described in Roberts et al (2002) *Adv Drug Deliv Rev* 54, 459-476, Bhadra et al., (2002) *Pharmazie* 57, 5-29, Kozlowski et al., (2001) *J Control Release* 72, 217-224, and Veronese (2001) *Biomaterials* 22, 405-417, all incorporated herein by reference.

The potential advantages of PEGylation of the compound of the invention include reduced renal clearance which, for some products, results in a more sustained adsorption after subcutaneous administration as well as restricted distribution, possibly leading to a more constant and sustained plasma concentrations and hence an increase in clinical effectiveness. Further potential advantages include reduced immunogenicity of the therapeutic compound, and lower toxicity.

The compound of the invention is one which is capable of binding to MAP kinase p38α. MAP kinase p38α is the human enzyme whose amino acid sequence (SEQ ID No: 18) is given in FIG. 1. Conveniently, the enzyme may be fused to a polypeptide sequence, such as a GST, that allows for its immobilisation on a solid substrate.

When the compound of the invention is a peptide, a suitable way of determining binding to MAP kinase p38α is to use phage display techniques. DNA encoding the peptide leads can be cloned into the M13 gpIII phagemid vector, transformed into *E. coli* TG1 cells and plated on 2% glucose, 2×TY, 100 µg/ml ampicillin plates. The colonies are grown for the production of phage particles as described (Scott & Smith (1990) *Science* 249, 386-390). For the assay, 1 µg MAP kinase p38α is coated onto MaxiSorp™ polystyrene plates (Nunc™ brand, Fisher Scientific, Loughborough, U.K.) in 100 µl PBS for 1 hour at room temperature and then washed once with PBS followed by blocking with 2% BSA in PBS for 1 hour at room temperature. 100 µl of phage supernatant is added per well and incubated for 1 hour at room temperature. The plates are washed four times with PBS/Tween20 and twice with PBS. The horseradish peroxidase-conjugated (HRP) anti-M13 secondary antibody (GE Healthcare U.K. Ltd., Chalfont St. Giles, U.K.) is diluted 1:5000 in 2% BSA in PBS and incubated for an hour at room temperature followed by washing as above. ELISA assays are performed as described (McGregor & Robins (2001) *Anal. Biochem.* 294, 108-117. The assay was developed with SureBlue TMB peroxidase substrate (Insight Biotechnology, Middlesex, U.K.) and read at 450 nm. The peptides that bound MAP kinase p38α are tested for specificity against biotinylated MAP kinase p38α and streptavidin and then against β-galactosidase, BclX, anti-FLAG M2 antibody, ovalbumin and lysozyme all coated at 0.5 µg in a streptavidin coated plate (StreptaWell; Roche Diagnostics Ltd., Burgess Hill, U.K.) using the same ELISA conditions as described above. This method can be used to establish direct specific peptide binding to MAP kinase p38α, and binding is indicated by an increased colorimeric signal over control background.

It is particularly preferred if the compound of the invention is one which competes for binding to MAP kinase p38α of a peptide with SEQ ID No:1 (all L-amino acids and containing peptide bonds between the amino acid residues, the peptide being N-acetylated ie BB2702). Whether or not a compound is one which can compete for binding to MAP kinase p38α of a peptide with SEQ ID No:1 can be determined as follows.

The N-acetylated peptide HKSRALLIFQKIMWLRRQ (SEQ ID No: 1) (ie BB2702) is labelled fluorescently (ie with a fluorophore) and is bound to MAP kinase p38α. Displacement of this peptide by a compound is indicative of binding of that compound to MAP kinase p38α, and can be measured by fluorescence polarization. Fluorescence polarization is an empirical fluorescence detection technique that measures the vertical and horizontal components of fluorescence emission created using plane polarized excitation. Polarization values (measured in mP units) for any fluorophore-labelled complex are inversely related to the speed of molecular rotation of that complex. Since molecular rotation is, in turn, inversely related to its molecular volume, the fluorescence-labelled peptide will possess a higher polarization value when it interacts with any molecule large enough to slow its rate of molecular rotation (MAP kinase p38α in this case). The magnitude of the polarization signal is thus used to quantitatively determine the extent of fluorescence-labelled peptide binding without the need for any filtration or wash separation step. The principle of this displacement binding assay is competition between the fluorescently labelled peptide and the unlabelled compound for binding to the MAP kinase p38α docking site, using a fluorescence polarization detection method. Binding of unlabelled compound causes displacement of the fluorescently labelled peptide and a loss of mP signal. Any loss of signal indicates displacement. A large loss of signal indicates greater displacement than a small loss of signal which indicates lower displacement. Any number of fluorescent polarisation readers can be used to measure displacement.

It is still further preferred if the compound of the invention is one which inhibits MAP kinase p38α. Inhibition of MAP kinase p38α may be determined as follows. Myelin basic protein (MBP) is a substrate of MAP kinase p38α and is phosphorylated in the presence of this enzyme and ATP. The phosphorylation event may be monitored using antibodies which recognise the phosphorylated serine or threonine residue, or by measuring the incorporation of radioactively labelled phosphate into the protein. Inhibition is measured by a decrease in the phosphorylation of MBP. BB2702 inhibits MAP kinase p38α directly and inhibits the activation of MAP kinase p38α. This can be seen by considering the activity of BB2702 against phosphorylated and nonphosphorylated MAP kinase p38α (see Table 3 in Example 9 below). The compound of the invention may inhibit the activation of MAP kinase p38α by MKK6.

It is particularly preferred if the compound of the invention is one which binds to and inhibits MAP kinase p38α, but does not substantially bind to and inhibit any of Jnnk, PKCd, p38b, AMPK, AurA, GK3b, RAF1, JNK3, VEGF, p38g, PKCb, PKCa, PDHK2, PDK1, MKK6, p27 KIP, Cdk2 KIP, Prak KIP, Chk1 KIP, Egfr KIP, Kdr KIP, EGF KIP, Zap 70 KIP, IGFR KIP, Src KIP, Fak KIP, Jak3 KIP, Akt CIRA, and Mek CCEK. Commercial services are available to determine whether a compound inhibits these and other protein kinases using standard methods. For example, Merck Millipore's Kinase Profiler™ may be used and version 54 of its Service Assay protocols.

Preferably, the compound of the invention has an $IC_{50}$ value of >1 μM, and more preferably >5 μM or >10 μM for at least one if not all of the enzymes listed to which it does not substantially bind.

It is preferred if the compound of the invention has an $IC_{50}$<1 μM against human MAP kinase p38α. It is more preferred if the compound of the invention has an $IC_{50}$<0.1 μM, preferably <0.05 μM, more preferably <0.01 μM, and still more preferably <0.001 μM, as measured using the following methodology. $IC_{50}$ is calculated by testing the degree of inhibition of a fixed concentration of MAP kinase p38α using increasing concentrations of the compound. When plotted on a log scale with the degree inhibition on the y axis and peptide concentration on the x-axis this will normally provide a sigmoid curve from 0% inhibition at the 0 or lowest concentration up to 100% inhibition at the highest doses. The point at which 50% inhibition is achieved is called the inhibitory concentration 50 or $IC_{50}$ and is used to establish the potency of a compound at a fixed concentration of enzyme.

As is discussed in more detail in Example 8, the compound HKSRALLIFQKIMWLRRQ (SEQ ID No: 1) (BB2702) has an $IC_{50}$ of 0.007 μM, and displays very high selectivity for MAP kinase p38α. Without being bound by any theory, the inventor believes that this high selectivity is due in part to the compound binding to a site on MAP kinase p38α which is not present in other protein kinases, and not to the ATP binding pocket. The site is believed to be conserved between human MAP kinase p38α and canine MAP kinase p38α. The ATP binding pocket is a conserved ATP binding pocket found in all protein kinases and also many ATP binding proteins, and so may be present in hundreds of proteins in the human (or canine) proteome. As the pocket is found in many different proteins, and as it is responsible for the binding of ATP, it is very challenging to produce selective inhibitory compounds which block ATP binding to the protein and thus prevent enzyme activity. On the other hand, sites outside of the active site are of much greater diversity and often only associated with a single target protein. Therefore, a site outside of the active site on MAP kinase p38α may be the only site of this nature in the human (or canine) proteome, with no significant homology with other such sites, and thus offers the chance of very high selectivity of compounds binding thereto. Thus, inhibition of MAP kinase p38α by the binding of a compound at an unusual, and possibly unique, binding pocket offers the much greater likelihood of selective inhibition of MAP kinase p38α and therefore avoiding off target side effects and toxicity.

A third aspect of the invention provides a method for inhibiting MAP kinase p38α the method comprising contacting the said kinase with a compound of the invention. Typically, the method is carried out in vitro. Thus, the compounds of the invention find uses as reagents for analysing MAP kinase p38α. The invention also includes a kit of parts for analysing MAP kinase p38α, the kit comprising a compound of the invention and a substrate for MAP kinase p38α. Suitable substrates for MAP kinase p38α include myelin basic protein (MBP), MK2/MAPKAPK2, MNK-1, PRAK, and MSK1. MBP is a preferred substrate. The invention therefore also includes use of a compound of the invention for inhibiting MAP kinase p38α.

Inhibition of MAP kinase p38α is known to be useful therapeutically, particularly in the treatment of inflammatory conditions. Thus, a fourth aspect of the invention provides the compounds of the invention for use in medicine to treat an individual. The individual may be a human or a non-human animal, such as a non-human mammal. Because of the degree of amino acid sequence similarity (99.4% identity) to human MAP kinase p38α (MK14_HUMAN SEQ ID No: 18) and canine MAP kinase p38α (MK14_CANFA SEQ ID No: 19) (see FIG. 1), the compounds are particularly suited for the treatment of man and dogs. The compounds of the invention may also be useful for treating other animals which have a MAP kinase p38α with substantial sequence similarity (eg >90% identity) to the human enzyme sequence.

The compounds may be used either alone or in combination with other therapeutic compounds. Thus, a fifth aspect of the invention provides a composition comprising a compound of the invention and one or more other therapeutic compounds, such as anti-inflammatory or anti-infective (eg anti-bacterial or anti-viral) or anti-proliferative compounds.

A sixth aspect of the invention provides a pharmaceutical composition comprising a compound of the invention, or the composition of the fifth aspect of the invention, and a pharmaceutically acceptable excipient or carrier. The excipient(s) and carrier(s) must be "acceptable" in the sense of being compatible with the compound of the invention and not deleterious to the recipients thereof. Suitable pharmaceutical excipients and carriers may be selected as known in the art depending on the route of administration for the compound or composition and whether the compound or composition is for human or veterinary use.

The compounds of the invention or a formulation thereof may be administered by any conventional method as discussed in more detail below. The treatment may consist of a single dose or administration or a plurality of doses or administrations over a period of time.

The formulation may be in a unit dosage containing a daily dose or unit, daily sub-dose or an appropriate fraction thereof, of the active ingredient.

The compounds of the invention will normally be administered topically or orally or by any parenteral route, in the form of a pharmaceutical formulation, optionally in the form of a non-toxic organic, or inorganic, acid, or base, addition salt, in a pharmaceutically acceptable form. Depending upon the disorder and individual to be treated, as well as the route of administration, the compositions may be administered at varying doses.

For example, the compounds of the invention can be administered orally, buccally, intranasally, intra-occularly, topically, rectally or sublingually in the form of tablets, capsules, ovules, elixirs, solutions or suspensions, which may contain flavouring or colouring agents, for immediate-, delayed- or controlled-release applications. The compounds of invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The compounds of the invention can also be administered parenterally, for example, intravenously, intra-arterially, intraperitoneally, intrathecally, intraventricularly, intrasternally, intrathoracically, intracranially, intra-muscularly, subcutaneously or intradermally, or they may be administered by infusion techniques. They may be used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

The compounds of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, eg sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains at least 1 μg of a compound of the invention for delivery to the patient. It will be appreciated that the overall daily dose with an aerosol will vary from patient to patient, and may be administered in a single dose or, more usually, in divided doses throughout the day.

Alternatively, the compounds of the invention can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route, particularly for treating diseases of the eye.

For ophthalmic use, the compounds of the invention can be formulated using nanoparticle systems or as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water. The compounds of the invention may also be formulated with nanoparticles which have proven tissue and cell penetration qualities.

Furthermore, for application topically, the compounds of the invention (whether alone or in combination with other active ingredients or materials) may be applied to, or impregnated into, a wound dressing so as to provide a dressing which can be used to treat an inflammatory condition or improve wound healing in an individual.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

The compounds of the invention may be delivered using an injectable sustained-release drug delivery system. These are designed specifically to reduce the frequency of injections. An example of such a system is Nutropin Depot which encapsulates recombinant human growth hormone (rhGH) in biodegradable microspheres that, once injected, release rhGH slowly over a sustained period.

The compounds of the invention can be administered by a surgically implanted device that releases the drug directly to the required site. For example, Vitrasert releases ganciclovir directly into the eye to treat CMV retinitis. The direct application of this toxic agent to the site of disease achieves effective therapy without the drug's significant systemic side-effects.

Electroporation therapy (EPT) systems can also be employed for the administration of peptides. A device which delivers a pulsed electric field to cells increases the permeability of the cell membranes to the drug, resulting in a significant enhancement of intracellular drug delivery.

Peptides can be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of peptide delivery is the ReGel injectable system that is thermo-sensitive. Below body temperature, ReGel is an injectable liquid while at body temperature it immediately forms a gel reservoir that slowly erodes and dissolves into known, safe, biodegradable polymers. The active drug is delivered over time as the biopolymers dissolve.

The compounds of the invention can be introduced to cells by "Trojan peptides". These are a class of polypeptides called penetratins which have translocating properties and are capable of carrying hydrophilic compounds across the plasma membrane. This system allows direct targeting of oligopeptides to the cytoplasm and nucleus, and may be non-cell type specific and highly efficient. See Derossi et al (1998), *Trends Cell Biol* 8, 84-87, incorporated herein by reference.

The amount of the compound of the invention to be administered to the individual may be determined by the medical practitioner (doctor or vet) and will depend on whether the individual is a human or animal (and the type of animal), the condition to be treated and the route and frequency of administration. Conveniently, the compound of the invention may be administered to the skin in carrier formulation so that from 10 µg to 100 mg in carrier formulation is delivered per 2 cm$^2$ of area of inflammation, for example 100 µg, 1 mg, 5 mg, 10 mg or 50 mg.

A seventh aspect of the invention provides a method for treating an inflammatory condition in an individual, the method comprising administering to the individual a compound of the invention or a composition of the fifth aspect of the invention. The individual may be administered the compounds of the invention and the other therapeutic compound either sequentially in any order or simultaneously.

An eighth aspect of the invention provides a compound of the invention, or a composition of the fifth aspect of the invention, for use in treating an inflammatory condition in an individual. In one embodiment, the individual may have been or is being or will be administered another therapeutic agent as discussed above.

A ninth aspect of the invention provides the use of a compound of the invention, or a composition according to the fifth aspect of the invention, in the manufacture of a medicament for treating an inflammatory condition in an individual. In one embodiment, the individual may have been or is being or will be administered another therapeutic agent as discussed above.

The inflammatory conditions to be treated include those in which the inflammatory pathway containing MAP kinase p38α plays a role in its pathology. Inflammatory conditions for treatment by the compounds of the invention include, but are not limited to, inflammatory disorders of the skin such as atopic dermatitis, psoriasis, acne vulgaris, dermal scarring. Activation of MAP Kinase p38α may also play a fundamental role in other disorders involving inflammation including, constrictive obstructive pulmonary disease, asthma, inflammatory bowel disease, atherosclerosis, cancer and rheumatoid arthritis, and these conditions may also be treated using the compounds of the invention. The inflammatory condition which is treated may be a temporary, regular or permanent condition experienced by an individual.

A tenth aspect of the invention provides a method for identifying a molecule that binds to MAP kinase p38α, the method comprising determining whether the molecule binds to MAP kinase p38α at the position that a compound of the invention binds to MAP kinase p38α.

Preferences for the compound for use in any of the third, fourth, fifth, sixth, seventh, eighth, ninth and tenth aspects of the invention are the same as for the compounds of the invention in the first and second aspects.

It is preferred that the compound used in the method of the tenth aspect of the invention is the peptide with amino acid sequence SEQ ID No: 1, although other compounds of the invention may be used.

The method of the tenth aspect of the invention may be used to identify molecules which are useful for selectively inhibiting MAP kinase p38α, and which are useful in anti-inflammatory therapy. There are various ways of identifying whether a test molecule binds to MAP kinase p38α at the same position as the peptide with amino acid sequence SEQ ID No: 1. One way is to conduct biochemical competition assays between the test molecule and a compound of the invention such as the peptide with amino acid sequence SEQ ID No: 1, or another compound of the invention, to determine whether the test molecule is able to displace the peptide with amino acid sequence SEQ ID No: 1, or another compound of the invention, from its binding site on MAP kinase p38α, for example by using the fluorescence polarization method discussed above. Typically, the peptide with amino acid sequence SEQ ID No: 1, or another compound of the invention, is labelled with a detectable, such as fluorescent, label. In another embodiment, an affinity-based assay, or an enzyme linked immunoassay (ELISA) are used. Another way is to use computational chemistry. High resolution structural information produced via X-ray crystallisation or 2 dimensional nuclear magnetic resonance may be used to build a precise computational model MAP kinase p38α and the precise docking of a peptide such as BB2702. The docking of the peptide reveals key interacting points that can then be used to computationally dock small molecules and other peptides. This will allow for the selection of compounds including peptides that may exploit the same pocket and key interacting surfaces without the need for screening many millions of compounds. Candidate molecules believed to have a high chance of inhibiting MAP kinase p38α can then be screened further, for example using a classic biochemical phosphorylation assay.

Once a molecule is identified, typically further analyses are carried out. For example, the following steps may be carried out: (a) determination of the $IC_{50}$ value of the molecule for MAP kinase p38α, (b) determining its effect on TNF stimulation in Hela cells, (c) NMR studies of the binding to MAP kinase p38α, (d) analysis of selectively towards MAP kinase p38α, (e) X-ray analysis of the molecule and (f) co crystallisation studies of the molecule and MAP kinase p38α, including X-ray diffraction studies.

Molecules which are identified may be synthesised and studied further. Preferred molecules are those which bind selectively to MAP kinase p38α, have an $IC_{50}$ of <1 µM, preferably <0.1 µM, more preferably <0.05 µM, still more preferably <0.01 µM and yet still more preferably <0.001 µM and do not substantially inhibit any of Jnnk, PKCd, p38b, AMPK, AurA, GK3b, RAF1, JNK3, VEGF, p38g, PKCb, PKCa, PDHK2, PDK1, MKK6, p27 KIP, Cdk2, Prak, Chk1, Egfr, Kdr, EGF, Zap 70, IGFR, Src, Fak, Jak3, Akt CIRA, and Mek. For example, preferred molecules are ones with an $IC_{50}$ value of >1 µM, and more preferably >5 µM or >10 µM for at least one if not all of the enzymes listed which the molecule does not substantially inhibit.

The method may further comprise the step of formulating the compound identified into a pharmaceutically acceptable composition. The invention also includes a method of making a pharmaceutical composition containing a molecule identified using the method of the tenth aspect of the invention the method comprising the step of mixing the so-identified molecule with a pharmaceutically acceptable carrier.

The invention will now be described in a non-limiting way by reference to the following Figures and Examples.

Figure 4:
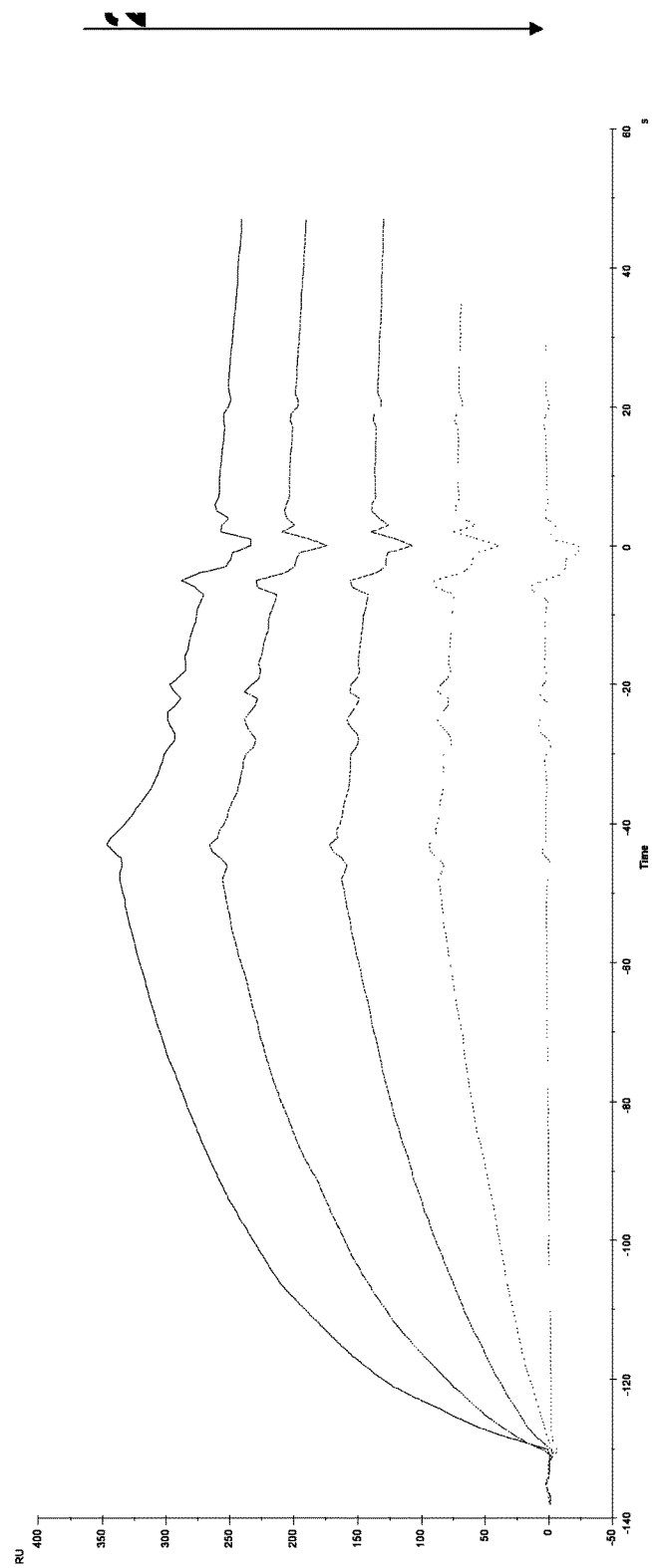
Figure 5:
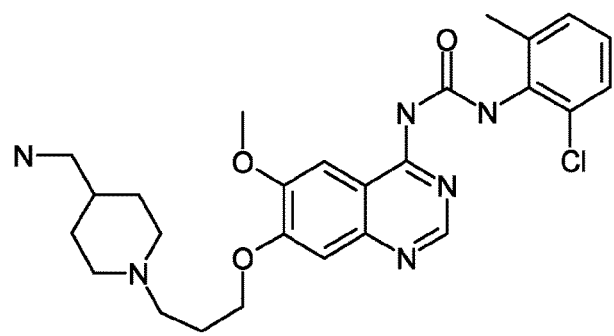

FIG. 1: Amino acid sequence alignment of human and canine MAP kinase p38α. There are 358 identical positions between human and dog sequence (99.44% identity);

FIG. 2: Alanine scanning data;

FIG. 3: Effect of BB2702 on basal phosphorylated MAP kinase p38α;

FIG. 4: Measurement of binding affinity using BIAcore analysis. OH-p38α binding to BB2702;

FIG. 5: Structure of ureidoquinazoline from WO 01/04102; and

Figure 6:
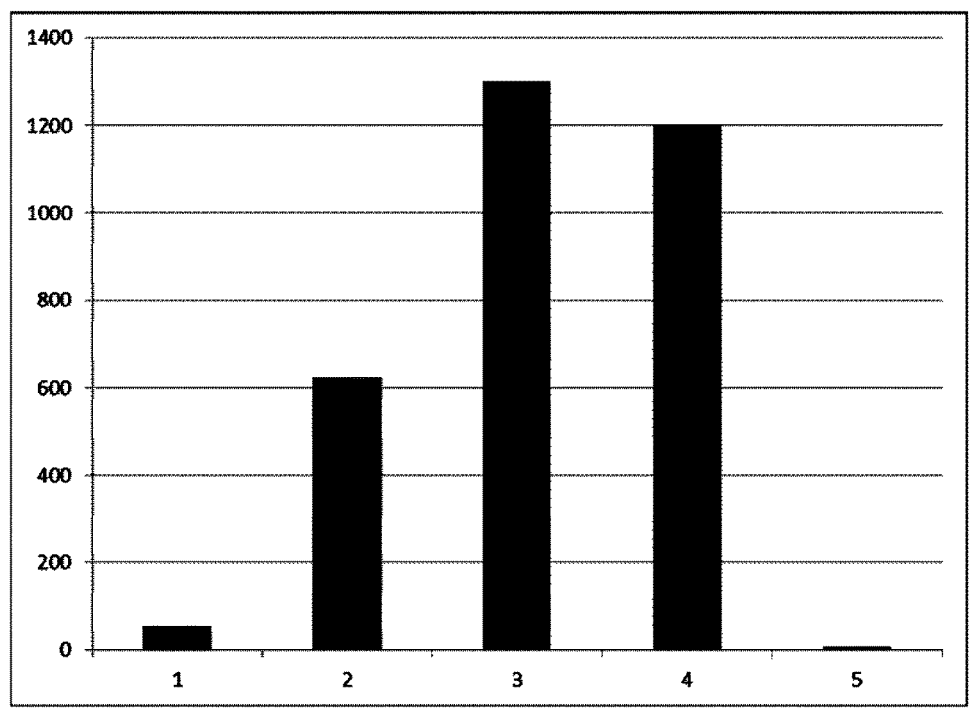

FIG. 6: Inhibition of TNFα production in LPS stimulated THP-1 cells by BB2702. X-axis is nM BB2702: 1=1000 nM; 2=100 nM; 3=10 nM; 5=no LPS stimulation. Y-axis TNFa production in µg/ml

EXAMPLE 1

Peptides

The following peptides were prepared using standard synthetic chemistry.

```
1. BB2700
                                    (SEQ ID No: 17)
   SRALLIFQKI
   (N-acetylated)

2. BB2702
                                    (SEQ ID No: 1)
   HKSRALLIFQKIMWLRRQ
   (N-acetylated)
```

EXAMPLE 2

Alanine Scanning Experiments

BB2702 amino acid sequence is: HKSRALLIFQKIMWLRRQ (SEQ ID No: 1), and it is N-acetylated. Alanine scanning allows a structure activity relationship of the peptide to be built. By sequentially replacing each amino acid of the active peptide with the smallest amino acid having a side chain, alanine, and testing the activity of the new peptide a picture of which amino acid residue positions are important for activity and which positions are not can be built. So for example, if we replace position 4 arginine with alanine we see a large negative impact on the ability of the new peptide to inhibit MAP kinase p38α. So we can conclude the position 4 arginine is an important interaction point of the peptide in the binding to and inhibition of MAP kinase p38α. As this is carried out for each of the 18 positions in the peptide BB2702 so we build up knowledge of the key residue sites on the peptide necessary for inhibition of p38α MAP kinase. Using this approach the key residues in the sequence for binding are shown. Those residues at positions in bold underlined below are very important for binding with high affinity to MAP kinase p38α and were determined by alanine scan experimentation and assessment of activity in a biochemical assay to evaluate ability to inhibit MAP kinase p38α. Those residues at positions in italic underlined are important but with smaller influence in binding.

H <u>K</u> S <u>R</u> A L L <u>*I*</u> <u>F Q</u> K I <u>*M*</u> W L <u>R</u> R Q  (SEQ ID NO: 1)

EXAMPLE 3

MAP Kinase P38α Assay

Materials
  MKK6
  GST-fusion protein expressed in *E. coli*. Stock solution 12 mg/ml. Store at −80° C. (MKK6 basal activity sufficient to activate P38α).
  MAP Kinase P38α
  6-his C-myc tagged protein expressed in *E. coli*. Stock solution 10 mg/ml. Store at −80° C.
  Myelin Basic Protein (MBP) (GibcoBRL 13228-010)
  25 mg dissolved in 3.75 ml Kinase buffer (with β-ME)
  γ$^{33}$P-ATP (Amersham AH9968 250 uCi)
  ATP (Sigma A-7699)
  1 mM stock in glass distilled water. Store at −80° C.
  Magnesium Acetate (Sigma M-0631)
  1M stock solution in water. Store at 4° C.
  Trichloroacetic acid (TCA) (Sigma 490-10)
  Prepare both a 20% and a 2% solution in water. Store at room temperature.
  Kinase Buffer
  0.1 mM EGTA (Sigma E-4378). 50 mM Tris/HCl pH 7.4 (Sigma T-4003). 0.1 mM Sodium Orthovanadate solution (Sigma S-6508). Store at 4° C. Immediately prior to use add 1 μl β-mercapto-ethanol (Sigma M-7522) per ml of buffer. [0.038 g (38 mg) EGTA (SIGMA E-4378). 7.58 μm TRIS/HCL pre-set PH 7.4 (SIGMA T-4003). 0.018 g (18 mg) Sodium Orthovanadate (SIGMA S-6508). Make up to 1 Litre in glass distilled water. Immediately prior to use add 1 μl β-mercapto-ethanol (Sigma M-7522) per ml of buffer. Store at 4° C.]
  96 Well Plates
  For use with DMSO (Corning incorporated (Costar) 3365 (polypropylene).
  Assay plates (Corning incorporated (Costar) 3596 (polystyrene—flat bottomed with lid).
  Filter plates (Cambarra Packard 6005174 (with bonded GF/C filter)).

EXAMPLE 4

MAP Kinase p38α Protocol (Version 1) (Enzyme Concentration 6.5 μg/ml)

Enzyme Activation
  Human MAP kinase p38α is activated prior to use by incubation with MKK6 for 3 hours at 30° C. The activation incubate contains 550 μl Kinase buffer, 75 μl (1 mM) ATP, 75 μl (100 mM) MgAc, 50 μl (10 mg/ml) P38α and 5 μl (12 mg/ml) MKK6. This activation incubate can be aliquoted and stored at −20° C.
Method
  Reference compound is SB203580 (IC$_{50}$=0.025 uM)
  Compounds made up at 10 mM in DMSO: Wt(mg)/MWt×100=Amount(ml) DMSO to be added).
  Serial dilutions are made in DMSO (1$^{st}$ dilution plate)
  In a 96 well plate (polypropylene).
  100 μl DMSO in all rows except the first row.
  50 μl compound in first well with DMSO.
  50 μl across the plate with mixing.
  These serial dilutions are then diluted 1:10 in kinase buffer (2$^{nd}$ dilution plate).
  In a 96 well plate (polystyrene).
  90 μl Kinase buffer in all rows necessary.
  10 μl compound dilutions (Row 3-1) (20 μM-0.006 μM (final concentration).
  10 μl of 10% DMSO in kinase buffer added to 'maximum' and 'minimum' control wells.
  Make up working enzyme solution: For each 96 well plate mix 2.50 ml Kinase buffer, 500 μl Myelin Basic Protein (6.66 mg/ml in Kinase buffer), and 50 μl activated P38α (activated enzyme is replaced by Kinase buffer in 'minimum' control wells). Add 30 μl to all test wells.
  Prepare Labelled ATP Solution:
  For each 96 well plate add 50 μl MgAc (1M) 900 μl distilled water, 50 μl ATP (1 mM) and 5 μCi (0.5-1 μl) γ $^{33}$P-ATP.
  Add 10 μl to all wells.
  Seal and incubate plate(s) at room temperature for 60 mins with gentle agitation (plate shaker).
  Stop the reaction with addition of 50 μl per well of 20% TCA solution. *100 ml TCA+400 ml milli Q water.
  Capture precipitated MBP on a filter plate using a micro-cell harvester. Use 2% TCA (approx 100 ml) to wash through plate and 0.75% Phosphoric acid (approx 100 ml) to end rinse the harvester. Leave plates to dry overnight.
  Add 25 μl Micro-scintillant to each test well and read on a topcount scintillation counter (counts per minute).

EXAMPLE 5

MAP Kinase 38α Protocol (Version 2) (Enzyme Concentration 0.5 ug/ml)

Enzyme Activation.
  Human MAP kinase p38α is activated prior to use by incubation with MKK6 for 3 hours at 30° C. The activation incubate contains 550 μl Kinase buffer, 75 μl (1 mM) ATP, 75 μl (100 mM) MgAc, 50 μl (10 mg/ml) P38α and 5 μl (12 mg/ml) MKK6. This activation incubate can be aliquoted and stored at −20° C.
Method
  Reference compound is SB203580 (IC50=0.025 uM)
  Compounds made up at 10 mM in DMSO.
  Wt(mg)/MWt×100=Amount(ml) DMSO to be added)
  Serial dilutions are made in DMSO (1$^{st}$ dilution plate)
  In a 96 well plate (polypropylene).
  100 μl DMSO in all rows except the first row.
  50 μl compound in first well with DMSO.
  50 μl across the plate with mixing.
  These serial dilutions are then diluted 1:10 in kinase buffer (2$^{nd}$ dilution plate).
  In a 96 well plate (polystyrene).
  90 μl Kinase buffer in all rows necessary.
  10 μl compound dilutions (Row 5-12) (2.22 μM-0.001 μM (final concentration)) transferred and mixed.
  10 μl transferred from dilution plate 2 to assay plates (in duplicate) (2% DMSO final concentration).
  10 μl of 10% DMSO in kinase buffer added to 'maximum' and 'minimum' control wells.
  Make up working enzyme solution: For each 96 well plate mix 2.55 ml Kinase buffer, 500 μl Myelin Basic Protein (6.66 mg/ml in Kinase buffer), and 3.8 μl activated P38α (activated enzyme is replaced by Kinase buffer in 'minimum' control wells). Add 30 μl to all test wells.
  Prepare Labelled ATP solution: For each 96 well plate add 50 μl MgAc (1M) 900 μl distilled water, 50 μl ATP (1 mM) and 5 μCi (0.5-1 μl) γ $^{33}$P-ATP.
  Add 10 μl to all wells
  Seal and incubate plate(s) at room temperature for 60 mins with gentle agitation (plate shaker).

Stop the reaction with addition of 50 μl per well of 20% TCA solution. *100 ml TCA+400 ml milli Q water.

Capture precipitated MBP on a filter plate using a microcell harvester. Use 2% TCA (approx 100 ml) to wash through plate and 0.75% Phosphoric acid (approx 100 ml) to end rinse the harvester. Leave plates to dry overnight.

Add 25 μl Micro-scintillant to each test well and read on a topcount scintillation counter (counts per minute).

EXAMPLE 6

Effect of BB2702 on Basal p38α Activity in Hela Cells

Hela cells are used to model certain aspects of the inflammatory response, such as cytokine production. In particular the production of TNFα, IL-1α, IL-1β, IL-6 and IL-8 inflammatory cytokines in response to lipopolysaccharides (LPS) or other proinflammatory stimuli. This can be via MAP kinase p38α dependent or independent means. Often the small molecule inhibitor of MAP kinases p38α SB203580 is used to explore the role of MAP kinase p38α in this inflammatory signalling cascade. FIG. 3 looks at the effect of BB2702 on basal phosphorylation status of p38α in Hela cells. Phospho p38α is the active form of the p38α capable of downstream signalling and resulting in production of inflammatory cytokines. We have demonstrated in Table 2 (in Example 8 below) that BB2702 inhibits p38α activation in a biochemical assay. Here we demonstrate that BB2702 depresses p38α phosphorylation in a cell model in the absence of any stimuli thus demonstrating reduced p38α activity in the presence of BB2702. We can conclude from this data that BB2702 is causing the suppression of basal p38α activity.

As is shown in FIG. 3, BB2702 reduces basal activated p38α. BB2702 prevents phosphorylation of MAP kinase p38α by its upstream activating kinase eg MKK6 or MKK3, or by autophosphorylation.

EXAMPLE 7

BIA Core Analysis of the Interaction Between BB2702 and MAP Kinase p38α

A Biacore 3000 was used to detect binding interactions using inhibition in solution assays (ISAs; Karlsson, R. (1994) Real-time competitive analysis of interactions between low-molecular-weight ligands in solution and surface immobilized receptors. *Anal. Biochem.* 221, 142-151). A target definition compound (a ureidoquinazoline compound, FIG. 5) that was known to bind to the purine site of kinases was immobilised on the sensor chip. The MAP kinase p38α was incubated with various concentrations of test compounds for 30 min and then allowed to flow over the sensor. Unbound p38α associated with the target definition compound giving a signal, which could be related to the free concentration. Dose-response data were analyzed to estimate $K_d$ values (eg 1 or 3, where $K_i'=K_d$), because competition by the target definition compound did not cause a significant shift in the midpoint. The target definition compound was immobilized by amine coupling onto a research-grade CM-5 chip using 7 min injections of a mixture of 11.5 mg/mL N-hydroxysuccinimide with 75 mg/mL 1-ethyl-3-(3-dimethylaminopropyl)carbodiimide hydrochloride, followed by 400 μM compound in 10 mM HEPES, pH 7.4, 0.15 M NaCl, 3.4 mM EDTA, 0.005% (v/v) surfactant P20, 4% (v/v) dimethyl sulfoxide, and finally 1 mM ethanolamine, pH 8.5, at a flow rate of 5 μL/min. Immobilization levels typically were around 3000 resonance units. A reference flow cell was prepared without the target definition compound. All measurements used a flow rate of 20 μL/min, and subtractions were made to eliminate refractive index change and injection noise. Surface regeneration was achieved by injecting 5 μL of 100 mM NaOH. The chip was calibrated with either nonphosphorylated or phosphorylated p38α using a report point of 60 s, when response was increasing linearly with time. Response was linear up to at least 400 nM protein. $K_d$ measurements were performed at 10-50 nM p38α, and confirmed to be 25 nM. This binding affinity is not incompatible with the biochemically derived Ki of 7 nM.

FIG. 4 shows the results of the BIA core analysis.

EXAMPLE 8

NMR studies of the binding of BB2702 to MAP kinase p38α

BB2702 ($IC_{50}$=1 nM) for inhibition of the activation of MAP kinase p38α by MKK6 shares a sequence motif (LIFQKI) SEQ ID NO: 24) in common with the PRK2-derived hydrophobic PDK1-interacting fragment or 'PIF'-pocket binding motif implicated in substrate kinase activation by PDK1 (Balendran et al (1999) *Curr. Biol.* 9, 393-402). In the crystal structure of PDK1 (Biondi et al (2002) *EMBO J.* 21(16), 4219-28), the αG helix of a symmetry-related PDK1 molecule occupies the hydrophobic motif binding pocket on the 'back' side of the catalytic domain N-terminal lobe, mimicking the intermolecular interaction with substrate kinases. However, MAP kinase p38αlacks an equivalent hydrophobic motif binding pocket: this region of the N-terminal lobe of MAP kinase p38αis instead occupied by its own C-terminal helix, so it seems unlikely that the potent binding of this BB2702 peptide to MAP kinase p38α is mediated via an equivalent interaction.

On the other hand, crystal structures of peptides from the MEF2A transcription factor and other substrates of MAP kinase p38α and, more recently, of the complex between MAP kinase p38α and MK2, have revealed that MAP kinase p38α possesses a substrate docking groove on the C-terminal lobe, proximal to the ATP binding site (Chang et al (2002) *Mol. Cell.* 9(6), 1241-9; ter Haar et al (2007) *J. Biol. Chem.* 282(13), 9733-9). We reasoned that this docking groove could be one possible site of interaction between the BB2702 and MAP kinase p38α, despite the lack of obvious sequence similarity with known MAP kinase p38α substrate kinase docking motifs. To investigate this, we used NMR to monitor the backbone amide chemical shift perturbations (CSPs) of the spectrum of MAP kinase p38α induced by binding of the BB2702 and MEF2A peptides. Sub-stoichiometric concentrations of BB2702 peptide induced chemical shift changes in the slow-exchange limit on the NMR time scale, consistent with high affinity (<1 μM) binding and, as expected, the shifts were essentially saturated at 1:1 stiochiometry (data not shown). Binding of the MEF2A peptide revealed a similar pattern of CSPs to those induced by BB2702 peptide: many of the same resonances of the kinase were affected, suggesting that the two peptides might share a similar, or overlapping, binding site. Furthermore, consistent with binding of the MEF2A peptide to the docking groove of the kinase, the CSPs were markedly different from those of small molecule ATP-competitive p38 inhibitors (Sullivan et al (2005) *Biochemistry* 44(50), 16475-90). However, in contrast to the BB2702 peptide, the binding of the MEF2A peptide is much weaker, with an estimated $K_d$ from NMR titration data of 250 μM. To probe further the relationship between the binding sites for MEF2A and BB2702 peptides, we then added BB2702 peptide to a sample of MAP kinase p38α with MEF2A peptide prebound. The BB2702 (240 μM) was able completely to displace the MEF2A peptide (5 mM), recapitulating the CSP pattern of BB2702 peptide binding alone (FIG. 5B). In contrast, and consistent with its weaker affinity, the MEF2A peptide (1 mM) was unable to displace BB2702 peptide (150 μM) as judged by unaltered CSPs, when the order of addition was reversed (data not shown). Taken together, the NMR data support the hypothesis that the BB2702 peptide may bind in, or close to, a groove on p38α used for docking with an upstream kinase regulator.

Experimental Details

BB 2702 was titrated into samples of uniformly $^{15}N,^{2}H$-labelled 6His-MAP kinase p38α(120μM) (Sullivan et al (2005) *Biochemistry* 44(50), 16475-90), either on its own or in addition to the MEF2A transcription factor-derived peptide (Chang et al (2002) *Mol. Cell.* 9(6), 1241-9) (RKPDL-RVVIPPSS) (SEQ ID NO: 25). $^{1}H$-$^{15}N$ TROSY-HSQC NMR spectra were acquired after each addition. NMR experiments were recorded at 298K on a 600 MHz Varian Inova spectrometer equipped with an HCN triple resonance cryoprobe as described in Sullivan et al (2005).

EXAMPLE 9

Selectivity of BB2702

Table 1 below compares the activity of 2 selected peptides and their ability to either inhibit the phosphorylation and therefore activation of p38α below MKK6 or MKK3. It also shows the ability of the coded peptides to inhibit activated p38α ability to phosphorylate a number of substrates. The data in the table shows that BB2702 inhibits the phosphorylation of p38α by MKK6 but not MKK3 moreover any active p38α is inhibited directly to prevent phosphorylation of either MBP or MK2. Thus BB2702 works by both inhibiting the activation of p38α and by inactivating active p38α.

Tables 2 and 3 (below): The ability of BB2702 to inhibit other protein kinases was evaluated by testing on over 30 protein kinase at 10 μM of peptide. This is the selectivity panel. Where inhibitors bind to the ATP binding pocket one can expect a lack of selectivity over this number of kinases. However, BB2702 is inactive against most the kinase targets up to 10 μM and indeed only see slight activity in 6 kinases but with overall 500 to 1000 fold selectivity when compared to p38α. The most active off target effect is against p38β a highly homologous family member of the MAPK family of kinases. However, even here the selectivity is over 100 fold. In summary we can conclude that BB2702 is extremely selective for p38α inhibition.

TABLE 1

| Peptide | IC50 μM MKK6/OH-p38α (ACTIVATION) | IC50 μM MKK6/OH-p38γ (ACTIVATION) | IC50 μ0M MKK3/OH-P38α (ACTIVATION) | IC50 μM P-p38a/MBP (ACTIVITY) | IC50 μM P-p38a/MK2 (ACTIVITY) | IC50 μM P-p38b/MBP V2 (ACTIVITY) |
|---|---|---|---|---|---|---|
| BB2700 | 0.075 (0.067-0.085) 0.277 (0.17-0.31) | >100 | >100 | 2.78 (1.9-4.1) | 0.9 (0.7-1.3) | 0.5 (with bg) 0.5 (with bg) |
| BB2702 | Very potent (out of range) 0.001 (0.004-0.016) | 6.8 (3-16) | 19.4 | 0.07 (0.049-0.1) | 0.02 (0.01-0.03) | 0.3 (with bg) 0.3 (with bg) |

Columns 2-4 show results from use of non-phosphorylated MAP kinase p38α, whereas columns 5-7 show results from use of phosphorylated MAP kinase p38α.

TABLE 2

| P38a Act. CCEK | Jnnk | PKCd | p38b | AMPK | AurA | GK3b | RAF1 | JNK3 | VEGF | p38g | PKCb | PKCa | PDHK2 | PDK1 | MKK6 | P38a KIP |
|---|---|---|---|---|---|---|---|---|---|---|---|---|---|---|---|---|
| 1 2.2 | | | | | | | | | | | | | | | | |
| 2 0.007 | >10 | >10 | >0.75 | >10 | >10 | >10 | >10 | >10 | >10 | >10 | >10 | >10 | >10 | ~10 | >10 | 0.150 |

Data as IC50 in μM, 1 = BB2700; 2 = BB2702n Tables 2 and 3 - columns 1 and 17 show MAP kinase p3α selectivity in the kinase selectivity panel.

TABLE 3

| P38a Act. | p27 | Cdk2 | Prak | Chk1 | Egfr | Kdr | EGF | Zap70 | IGFR | Src | Csk | Fac | Jak3 | Akt | Mek | P38a |
|---|---|---|---|---|---|---|---|---|---|---|---|---|---|---|---|---|
| 1 2.2 | | | | | | | | | | | | | | | | |
| 2 0.007 | >10 | >10 | >10 | >10 | 4 | 7 | >10 | 4 | 0.75 | >10 | 3 | >10 | 7 | ~10 | >10 | 0.150 |

Data as IC50 in μM, 1 = BB2700; 2 = BB2702

EXAMPLE 10

Inhibition of TNFα Production in LPS Stimulated THP-1 Cells by BB2702

FIG. 6 illustrates that when THP-1 cells are treated with BB2702 in a dose dependent manner and then stimulated by LPS (lipopolysaccharide) there is a significant reduction in the production of TNFα, an inflammatory cytokine known to be downstream of p38α. This demonstrates that BB2702 can inhibit inflammatory signalling mediated by p38α in the accepted THP-1 cell inflammation model.

THP-1 cells were pre-incubated with various doses of BB2702 (1, 10, 100 1000 nM) prior to stimulation with LPS (10 μg/mL) for 5 hours. TNF-α in cell supernatants was determined in duplicate by ELISA. Data is presented as the mean of 5 experiments each carried out in duplicate. The standard deviation for each falls within 15% of the mean.

The invention claimed is:

1. A compound comprising the amino acid sequence HKSRALLIFQKIMWLRRQ (SEQ ID No: 1) or comprising a part of said amino acid sequence of 10 or more contiguous amino acids, or comprising a variant of said amino acid sequence or of said part thereof in which from 1 to 2 amino acids have been altered, wherein the residues of positions 2, 4, 8, 9, 10, 13 and 16 are conserved as compared to SEQ ID NO: 1 when said positions are present in said variant or in said part thereof, and wherein the compound binds to MAP kinase p38α, and wherein the compound has a molecular weight of less than 25,000 daltons.

2. A compound according to claim 1, wherein the amino acid sequence is selected from: HKSRALLIFQKIMWLRR (SEQ ID No: 2), HKSRALLIFQKIMWLR (SEQ ID No: 3), HKSRALLIFQKIMWL (SEQ ID No: 4), HKSRALLIFQKIMW (SEQ ID No: 5), KSRALLIFQKIMWLRRQ (SEQ ID No: 6), SRALLIFQKIMWLRRQ (SEQ ID No: 7), SRALLIFQKIM (SEQ ID No: 8), SRALLIFQ (SEQ ID No: 9), HALAIFQKIMW (SEQ ID No: 10), HKSRALAIFQKIMALRRQ (SEQ ID No: 11), AKSRALLIFQKIMWLRRQ (SEQ ID No: 12), HKSRAALIFQKIMWLRRQ (SEQ ID No: 13), HKSRALLIFQKIMWARRQ (SEQ ID No: 14), HKSRALLIFQKIMWLRAQ (SEQ ID No: 15), HKSRALLIFQKIMWLRRA (SEQ ID No: 16) and SRALLIFQKI (SEQ ID No: 17).

3. A compound according to claim 1 which contains at least one non-peptide linkage between amino acids.

4. A compound according to claim 1 which contains at least one D-amino acid residue.

5. A compound according to claim 1 wherein the N- and/or C- terminal residue is blocked.

6. A compound according to claim 1 wherein the compound is a peptide joined to another moiety.

7. A compound according to claim 1 which is substantially resistant to protease digestion.

8. A composition comprising a compound according to claim 1 and one or more further therapeutic compounds selected from anti-inflammatory, anti-infective, anti-bacterial, and anti-proliferative compounds.

9. A pharmaceutical composition comprising a compound according to claim 1, and a pharmaceutically acceptable excipient or carrier.

10. A method for inhibiting MAP kinase p38α, the method comprising contacting the said kinase with a compound according to claim 1.

11. A method for treating an inflammatory condition in an individual, the method comprising administering to the individual a compound according to claim 1.

12. A method for identifying a molecule that binds to MAP kinase p38α, the method comprising determining whether the molecule binds to MAP kinase p38α at the position that a compound according to claim 1 binds to MAP kinase p38α.

13. A method according to claim 12, further comprising the step of formulating the molecule identified into a pharmaceutically acceptable composition.

14. A method of making a pharmaceutical composition comprising carrying out the method of claim 12 and the step of mixing the molecule identified with a pharmaceutically acceptable carrier.

15. A compound consisting of:
    the amino acid sequence HKSRALLIFQKIMWLRRQ (SEQ ID No: 1),
    or a part of said amino acid sequence of 8 or more contiguous amino acids,
    or a variant of said amino acid sequence or said part thereof in which from 1 to 2 amino acids have been altered, wherein the residues of positions 2, 4, 8, 9, 10, 13 and 16 are conserved as compared to SEQ ID NO: 1, when said positions are present in said variant or in said part thereof,
    and wherein the compound binds to MAP kinase p38α.

16. A compound according to claim 15, wherein the amino acid sequence is selected from: HKSRALLIFQKIMWLRR (SEQ ID No: 2), HKSRALLIFQKIMWLR (SEQ ID No: 3), HKSRALLIFQKIMWL (SEQ ID No: 4), HKSRAL-LIFQKIMW (SEQ ID No: 5), KSRALLIFQKIMWLRRQ (SEQ ID No: 6), SRALLIFQKIMWLRRQ (SEQ ID No: 7), SRALLIFQKIM (SEQ ID No: 8), SRALLIFQ (SEQ ID No: 9), HALAIFQKIMW (SEQ ID No: 10), HKSRALAIFQKIMALRRQ (SEQ ID No: 11), AKSRALLIFQKIMWLRRQ (SEQ ID No: 12), HKSRAALIFQKIMWLRRQ (SEQ ID No: 13), HKSRALLIFQKIMWARRQ (SEQ ID No: 14), HKSRALLIFQKIMWLRAQ (SEQ ID No: 15), HKSRALLIFQKIMWLRRA (SEQ ID No: 16) and SRALLIFQKI (SEQ ID No: 17).

17. A compound according to claim 15 which consists of the amino acid sequence HKSRALLIFQKIMWLRRQ (SEQ ID No: 1).

18. A method for inhibiting MAP kinase p38α, the method comprising contacting the said kinase with a compound according to claim 15.

19. A method for identifying a molecule that binds to MAP kinase p38α, the method comprising determining whether the molecule binds to MAP kinase p38α at the position that a compound according to claim 15 binds to MAP kinase p38α.

20. A method according to claim 19, further comprising the step of formulating the molecule identified into a pharmaceutically acceptable composition.

21. A method of making a pharmaceutical composition comprising carrying out the method of claim 19 and the step of mixing the molecule identified with a pharmaceutically acceptable carrier.

* * * * *